United States Patent [19]
Wood et al.

[11] Patent Number: 5,332,569
[45] Date of Patent: Jul. 26, 1994

[54] HAIR CARE COMPOSITION FOR CONDITIONING HAIR WITH SILICONE OIL

[75] Inventors: James L. Wood, Elmhurst; Andrea Mariahazy, Westchester, both of Ill.

[73] Assignee: Alberto-Culver Company, Melrose Park, Ill.

[21] Appl. No.: 65,212

[22] Filed: May 20, 1993

Related U.S. Application Data

[63] Continuation-in-part of Ser. No. 861,319, Mar. 31, 1992, abandoned.

[51] Int. Cl.$^5$ .......................... A61K 7/06; A61K 7/00
[52] U.S. Cl. ...................................... 424/70; 424/401; 514/937
[58] Field of Search .................... 424/70, 71; 514/937, 514/938, 941

[56] References Cited

U.S. PATENT DOCUMENTS

| | | | |
|---|---|---|---|
| 4,387,090 | 6/1983 | Bolich | 424/70 |
| 4,493,824 | 1/1985 | Abe | 424/70 |
| 4,960,845 | 10/1990 | O'Lenick | 528/25 |
| 5,070,171 | 12/1991 | O'Lenick | 528/33 |
| 5,078,991 | 1/1992 | Birtwistle et al. | 424/70 |

FOREIGN PATENT DOCUMENTS 0155806 9/1985 European Pat. Off. .
0126209 5/1985 Japan .

OTHER PUBLICATIONS

CTFA International Cosmetic Ingredient Dictionary, (1991) p. 377.

*Primary Examiner*—Thurman K. Page
*Assistant Examiner*—Sally Gardner
*Attorney, Agent, or Firm*—Tilton, Fallon, Lungmus & Chestnut

[57] ABSTRACT

A liquid hair care composition for conditioning hair with silicone oil comprises a stable emulsion of a water-insoluble hair conditioning silicone oil dispersed in a liquid carrier composed essentially of polyoxyalkylene glycol and an effective emulsifying amount of a complex formed from (i) an anionic copolymer of dimethylpolysiloxane and polyoxyethylene wherein the siloxane chain contains from 20 to 40 dimethylsiloxy units and the oxyethylene chain contains from 3 to 15 oxyethylene units and terminates in an anionic phosphate or sulfate group, and (ii) a cationic hair conditioner compound containing at least one cationic quaternary nitrogen or amido amine group and at least one hydrophobic aliphatic or silicone polymer chain.

16 Claims, No Drawings

HAIR CARE COMPOSITION FOR CONDITIONING HAIR WITH SILICONE OIL

RELATED APPLICATION

This application is a continuation-in-part of copending application Ser. No. 07/861,319, filed Mar. 31, 1992, now abandoned.

FIELD OF INVENTION

The field of this invention is hair treating compositions including hair conditioning emulsions and shampoo emulsions. More particularly, this invention relates to hair care emulsions containing silicone oils.

BACKGROUND OF INVENTION

The term "silicone oil" is used herein to designate water-insoluble silicone polymers which are applied to hair to improve its feel or appearance. Silicone oils can provide the hair with a silky, lubricious feel. They can also provide a lusterization effect. These results are obtained by coating hair strands with thin films of silicone oil. Since silicone oils are substantially water-insoluble, after application to the hair they tend to remain thereon. Silicone oil can be applied in a shampoo, or in a hair conditioner which is applied after shampooing and followed by water-rinsing. (See, for example, U.S. Pat. Nos. 4,704,272, 3,964,500, 5,034,218 and 4,387,090).

The two most common types of hair conditioning silicone oils are referred to in the International Cosmetic Ingredient Dictionary (CTFA) as "dimethicone" and "dimethiconol". Dimethicone is defined as a mixture of fully methylated linear siloxane polymers end blocked with trimethylsiloxy units. Dimethiconol is a dimethyl silicone polymer terminated with hydroxyl groups. Such hair conditioning silicone oils are relatively non-volatile liquids, which are obtainable from commercial sources in the United States and other countries. For example, silicone fluids are sold by Dow Corning Corporation, Midland, Mich. Among the silicone oils (also called fluids) supplied by Dow Corning for use in hair treating compositions is a solution of high-viscosity dimethiconol fluid in dimethicone (Dow Corning Q2-1403 Fluid).

Since silicone oils have limited solubility in water and other polar solvents, they are usually applied in the form of dispersions or emulsions. For example, in a water-based shampoo or hair conditioner, the silicone oil may be dispersed with the aid of an emulsifying agent, and the dispersion or emulsion may be stabilized by the inclusion of thickeners.

Cationic hair conditioning agents are commonly used in hair conditioning compositions, and to a lesser extent in shampoo formulations. Typically, cationic hair conditioning agents contain one or more cationic quaternary nitrogen or amido amine group, and one or more hydrophobic long chain aliphatic or silicone polymer. The cationic group can provide a degree of substantivity between the conditioning agent and hair. The long chain hydrophobic groups, which are derived from long chain fatty acids or are silicone polymers, can provide hair conditioning or hair repair functions.

The published European patent application 0 115 806 describes a hair conditioning composition containing silicone oil dispersed in water. The composition also contains dimethicone copolyol, which the Cosmetic Dictionary defines as a polymer of dimethylpolysiloxane with polyoxyethylene and/or polyoxypropylene side chains. To provide a stable emulsion, the composition is in the form of a gel vehicle, consisting of a lipid material and a cationic surfactant.

Silicone polymers having an anionic functional group, such as a phosphate or sulfate, have heretofore received only limited use in hair conditioning compositions, and are not known to have been used with silicone oil. Methods of preparation and chemical structure of sulfated silicone polymers and phosphated silicone polymers have been disclosed, respectively, in U.S. Pat. Nos. 4,960,845 and 5,070,171. The base polymer is a dimethicone copolyol since it contains a dimethylpolysiloxane chain with a side chain of polyoxyalkylene. The sulfate or phosphate group forms the terminus of the polyoxyalkylene side chains. The end hydroxyls have been converted to ester linkages to the sulfate or phosphate groups.

Hair Conditioning lotions are conventionally formulated as aqueous solutions, dispersions or emulsions. Organic solvents are not ordinarily used as carriers for the hair treating agents. Organic liquids may be included in the total formula as emulsifiers or hair conditioners. For example, U.S. Pat. No. 4,493,824 describes a water-based hair rinse containing a minor amount of polyethylene glycol.

SUMMARY OF INVENTION

The liquid hair care composition of this invention comprises a novel formulation for conditioning hair with silicone oil. To provide a stable emulsion of the water-insoluble silicone oil, it is dispersed in an organic solvent-base carrier. The carrier in which the silicone oil can be effectively emulsified and stabilized is composed of polyoxyalkylene glycol and an anionic-cationic emulsifier. The anionic component of the emulsifier comprises an anionic copolymer of dimethylpolysiloxane and polyoxyethylene wherein the siloxane chain contains from 20 to 40 dimethylsiloxy units and the oxyethylene chain contains from 3 to 15 oxyethylene units and terminates in an anionic phosphate or sulphate group. The cationic component of the emulsifier comprises a cationic hair conditioner which contains at least one cationic quaternary nitrogen or amido amine group and at least one hydrophobic aliphatic or silicone polymer chain. The liquid carrier may be polyoxyethylene glycol or a copolymer of polyoxyethylene and polyoxypropylene. The glycol comprises the major component of the formulation. A sufficient amount of emulsifier complex is employed to form a stable emulsion of the silicone oil in the glycol.

DETAILED DESCRIPTION

A key ingredient for preparing the formulations of this invention is an anionic emulsifier that is a copolymer of dimethylpolysiloxane and polyoxyethylene. These anionic dimethicone copolyols have polyoxyethylene chains terminating in an anionic phosphate or sulfate group. They can be prepared as described, respectively, in U.S. Pat. Nos. 4,960,845 and 5,070,171, or they can be obtained commercially from Phoenix Chemical, Inc., Somerville, N.J., and/or Siltech, Inc., Norcross, Ga. Phoenix Chemical sells dimethicone copolyol phosphates under its trademark "Pecosil".

For use in the emulsifier system of this invention, the siloxane chain functions as a hydrophobic moiety while the oxyethylene chain functions as a hydrophilic moiety. The hydrophobic-hydrophilic balance between these chains is of importance in achieving a high level of emulsifier activity. A desirable balance is obtained when the siloxane chain contains from 20 to 40 dimethylsiloxane units and the oxyethylene chain contains from 3 to 15 oxyethylene units. In preferred embodiments, the siloxane chain has from 25 to 35 dimethylsiloxane units and the oxyethylene chain has from 4 to 10 oxyethylene units. These ranges refer to average or representative chain lengths. It will be understood that not all of the co-polymer molecules have identical chain lengths. A representative commercial product which can be used for this invention is sold by Phoenix Chemical and Siltech as "Pecosil PS-100". It is estimated that the siloxane chain of this product contains on the average of around 32 dimethylsiloxane units and that the oxyethylene chain contains on the average around 7 oxyethylene units. The oxyethylene chain terminates in an ester-linked phosphate group which is in free acid form. The phosphate or sulfate groups may be in free acid form, while in some formulations preferably in neutralized form as water-soluble salts. The following type formulas are believed to be generally representative of the phosphate and sulfate group structures.

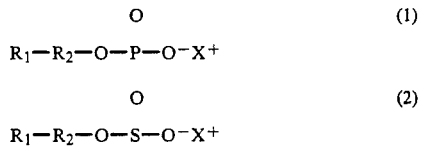

In the foregoing formulas, $R_1$ represents the dimethylpolysiloxane polymer, and $R_2$ represents the polyoxyethylene chain, which is connected by ester oxygen to the phosphorus or sulfur atom. The $R_2$ may be a side chain from $R_1$, or it may be linearly connected to a terminal dimethyl siloxy group. The letter X represents hydrogen when the phosphate or sulfate groups are in free acid form, or it may be a metal atom such as sodium, potassium, or lithium, or it may be ammonium, that is, $Na^+$, $K^+$, $Li^+$, or $NH_4^+$. Sodium salts are preferred. In some embodiments, the base siloxane polymer may have multiple side chains of polyoxyethylene. If such compounds are employed for the purpose of this invention, the total of the oxyethylene units should correspond with the ranges set out above.

As the cationic component of the emulsifier complex, a cationic hair conditioner compound is employed which contains at least one, but usually not more than two cationic quaternary nitrogen or amido amine groups, and also at least one or more hydrophobic aliphatic chains, or silicone polymer chains. The cationic component can be quaternary nitrogen-containing silicone polymers, or fatty quaternary nitrogen compounds. Fatty amido amine compounds are particularly desirable. The term "fatty" designates alkyl or alkylene residues of fatty acids such as particularly $C_8$ to $C_{22}$ saturated or unsaturated fatty acids. Fatty amido amines in dimer form can be used providing a combination of two long chain fatty groups and two amido amine groups. Such compounds may contain an aliphatic chain of up to 36 carbons.

Compounds containing both aliphatic and siloxy chains may be used, such as Siltech Silquat Q-100, which is a fatty monoquaternary silicone polymer. Amido amine hair conditioners that are commercially available include cocamido-propyl dimethylamine and lauramidopropyl dimethylamine. A preferred co-emulsifier is dilinolamidopropyl dimethylamine. A product of this kind is sold under the trademark "Catemol 360" by Phoenix Chemical, Inc., Somerville, N.J. Catemol 360 is understood to contain a dimerized chain of $C_{18}$ fatty groups, and has the general formula $(C_5H_{13}N_2)_2$ $C_{36}H_{66}O_2$. Fatty amido amines which can be used are obtainable from several sources, some of which include Croda, Inc. , New York, N.Y., Inolex Chemical Co., Philadelphia, Pa. and Scher Chemicals, Inc., Clifton, N.J. Quaternary silicones are available from Siltech,, Inc., Norcross, Ga., being sold under the trademark name "Silquat". One especially suitable product is "Silquat Q-100", which is water dispersible. Water-soluble forms are also available from Siltech, such as "Silquat Q-200 or Q-300".

Cationic hair conditioning agents of the kind which can be employed as co-emulsifiers in the formulations of this invention are described in U.S. Pat. No. 4,387,090 with reference to column 3 and 4 thereof. They comprise quaternary ammonium salts containing from 1 to 3 long chain fatty groups and 1 to 3 methyl groups. The di- or tri- fatty ammonium compounds are preferred.

Water-insoluble, non-volatile silicone oils (also sometimes called silicone fluids) are well known in the cosmetic arts, and are available through a number of commercial sources in the United States and other countries. They are extensively described in the patent literature. For example, reference may be had to U.S. Pat. No. 4,704,272, and the description of non-volatile silicone fluids found in columns 4 and 5 thereof. Such silicone oils or fluids can be obtained in the United States from the Dow Corning Corporation, Midland, Mich., and other companies such as Siltech, Inc., Norcross, Ga. A particularly suitable product is Dow Corning Q2-1403 Fluid, which is a solution of high-viscosity dimethiconol fluid and dimethicone.

In complete hair conditioner formulations, water-dispersible or water-soluble silicone polymers can also be used. For example, dimethicone copolyols may be used as auxiliary ingredients. Representative examples are Dow Corning 193 surfactant and Siltech "Silwax WS".

For the purpose of preparing stable emulsions the preferred liquid carrier is polyoxyalkylene glycol. In particular, polyoxyethylene glycol carriers are desirable. Alternatively, the carrier may comprise a copolymer of polyoxyethylene and polyoxypropylene. Polyoxyethylene liquids suitable for use in complete formulations of this invention are available from Phoenix Chemical, Inc., Somerville, N.J., under the trademark name "Phoenoxide". A suitable example is "Phoenoxide E-400". Similar products are available from Union Carbide Corp., Danbury, Conn., under the trademark name "Carbowax". In the Cosmetic Dictionary, they are referred to by the initials "PEG", for example, PEG-8 corresponds with "Phoenoxide E-400". That product has an average molecular weight of about 400. While polyoxyethylene products are available in molecular weights from 200 to 20,000, for purpose of the present invention, lower molecular weight products are preferred which have molecular weights in the range from 200 to 600. Instead of a polyoxyethylene carrier, carriers composed of polyoxyethylene chain in combination with polyoxypropylene chains can be used. These products are available from BASF Wyandotte Corp., Parsippany, N.J., under the trademark name "Pluronics". The particular polyoxyalkylene carrier selected will depend on the desired viscosity of the complete composition.

When a relatively low molecular weight carrier is selected, the viscosity may be increased and a thickening action obtained by using it in admixture with a polyoxyalkylene liquid of higher viscosity. For example, when the primary carrier is PEG-8, PEG-350 may be used as a thickener, being a product obtainable from Union Carbide as "Carbowax 20M".

As it is well known in the cosmetic arts, complete formulations may also include other compounds which have desirable hair conditioning properties. For example, AMP-isostearoyl hydrolyzed soy protein can be used. The product is defined in the Cosmetic Dictionary as the aminomethylpropanol salt of the condensation product of isostearic acid chloride with hydrolyzed soy protein. It is available from Kato Worldwide, Ltd., Mount Vernon, N.Y., as Natural Blend 23.

PRACTICE OF INVENTION

In practicing the invention, a sufficient amount of the cationic component of the emulsifier complex can be admixed with the anionic component emulsifier to substantially completely complex the anionic groups of the dimethicone copolyol phosphate or sulfate. However, since the cationic co-emulsifier has desirable properties as a hair conditioner, it can be present in molecular excess. Further, exact molar equivalency is not required. On a molecular basis, preferred proportions are from about 0.8 to 1.2 moles of cationic co-emulsifier per mole of anionic emulsifier. The amount of complex formed from the anionic-cationic components should be sufficient to emulsify the silicone oil in the polyoxyalkylene liquid base.

Starting with a pre-formed a mixture of the anionic and cationic components, the complex mixture can be introduced into the polyoxyalkylene carrier. Silicone oil can then be gradually added, and thereby being dispersed and emulsified. For complete formulations on a percent by weight basis from 1 to 10% of silicone oil can be used. The quantity of silicone oil should not exceed the amount for which a stable emulsion is obtained. On a total formula basis, preferred amounts of silicone oil are in the range from about 3 to 7 parts by weight per hundred parts of the conditioning formulation.

The polyoxyalkylene glycol carrier preferably is the major component of the formulation. For example, the complete formulation may contain from 60 to 90–98 parts by weight of the carrier per hundred parts of formulation.

A representative generalized formula for preparing hair conditioning emulsions in accordance with the present invention is set out below.

| General Formulation | |
|---|---|
| Ingredients | Parts by Wt. |
| Anionic Cationic/ Emulsifier Complex[a] | 1–10 |
| Silicone Oil[b] | 1–10 |
| PEG Carrier[c] | 60–98 |

[a]Dimethicone copolyol phosphate (or sulfate) on approximately equal molar basis with cationic co-emulsifier.
[b]Water-insoluble non-volatile dimethicone and/or dimethicone and/or dimethiconol polymer.
[c]Polyoxyethylene glycol of MW 200–20,000.

The following examples provide further information for practicing the invention.

EXAMPLE I

To a suitable mixing vessel is added 80 pounds of PEG-8 (Phoenix Phoenoxide E-400). Temperature is maintained at 160° F. to assure fluidity of the polyoxyethylene glycol. In a separate tank, 10 pounds of dimethicone copolyol phosphate (Phoenix Chemical Pecosil PS-100) is mixed with 5 pounds of dilinolamidopropyl dimethylamine (Phoenix Chemical Catemol 360) and 5 pounds of Quaternium-80 (Siltech Silquat Q-100). After this pre-mix has been formed, 5 pounds of a 60,000 cps high-viscosity dimethiconol (Siltech F-350) are added. The contents are heated to 160° F. with agitation, and mixed until a transparent or translucent emulsion is obtained. The resulting pre-mixed, preheated mixture is added to the heated Phoenoxide E-400 with agitation, the agitation being continued until a finely dispersed stable emulsion is obtained.

EXAMPLE II

In this example, a single tank preparation method is used. The tank is equipped with an agitator and heating means. To the tank, there is introduced 70 pounds of PEG-8 (Phoenix Chemical Phoenoxide E-400), and this liquid carrier is heated to a temperature of about 160° F. To the carrier is added 3.0 pounds of dimethicone copolyol phosphate (Phoenix Chemical Pecosil P-100), and mixing is continued at 160° F. for about 20 minutes, or until the silicone phosphate is completely dissolved. Next is added 3.0 pounds of dilinolamidopropyl dimethylamine (Phoenix Chemical Catemol 360). Stirring is continued at the same temperature for 20 minutes or until the amido amine co-emulsifier is completely dissolved. The emulsifier combination in the carrier is then ready for addition of water-insoluble silicone fluid. For example, 5 pounds of dimethicone/dimethiconol (Dow Corning Fluid Q2-1403) is added with rapid stirring while maintaining a temperature of about 160° F. Stirring is continued for 20 minutes or until the silicone fluid is completely dispersed and a homogeneous mix has been obtained. The resulting mix will comprise a stable emulsion of the silicone fluid. Thereafter, additional hair conditioning ingredients can be added, such as Quaternium-80, dimethicone copolyol, etc. For the addition of some of these ingredients, it may be desirable to reduce the temperature of the mix.

EXAMPLE III

A complete formulation is prepared following the procedure of Example II, and using the following formulation

| Ingredients | Weight Percent |
|---|---|
| PEG-8 (Phoenix Chemical Phoenoxide E-400) | 70.5 |
| PEG-350 (Union Carbide Carbowax 20M) | 3.0 |
| Dimethicone Copolyol Phosphate (Phoenix Chemical Pecosil PS-100) | 3.0 |
| Dilinolamidopropyl Dimethylamine (Phoenix Chemical Catemol 360) | 3.0 |
| Dimethicone (and) Dimethiconol (Dow Corning Fluid Q2-1403) | 5.0 |
| Siltech Silquat Q-100 | 5.0 |
| Dimethicone Copolyol (Dow Corning 192 Surfactant) | 5.0 |
| Dimethicone Copolyol (Siltech Silwax WS) | 5.0 |
| Amp-Isostearoyl Hydrolyzed Soy | 0.5 |

| Ingredients | Weight Percent |
| --- | --- |
| Protein, etc. (Kato Worldwide Natural Blend 23) | 5 |

EXAMPLE IV

To a suitable mixing vessel is added 80 pounds of PEG-8 (Phoenix Phoenoxide E-400). Temperature is maintained at 160° F. to assure fluidity of the polyoxethylene glycol. In a separate tank, 10 pounds of dimethicone copolyol sulphate (Siltech S-100) is mixed with 5 pounds of dilinolamidopropyl dimethylamine (Phoenix Chemical Catemol 360) and 5 pounds of Quaternium-80 (Siltech Silquat Q-100). After this pre-mix has been formed, 5 pounds of a 60,000 cps high-viscosity dimethiconol (Siltech F-350) are added. The contents are heated to 160° F. with agitation, and mixed until a transparent or translucent emulsion is obtained. The resulting pre-mixed, preheated mixture is added to the heated Phoenoxide E-400 with agitation, the agitation being continued until a finely dispersed stable emulsion is obtained.

EXAMPLE V

In this example, a single tank preparation method is used. The tank is equipped with an agitator and heating means. To the tank, there is introduced 70 pounds of PEG-8 (Phoenix Chemical Phoenoxide E-400), and this liquid carrier is heated to a temperature of about 160° F. To the carrier is added 3.0 pounds of dimethicone copolyol sulphate (Siltech S-100), and mixing is continued at 160° F. for about 20 minutes, or until the silicone sulphate or phosphate is completely dissolved. Next is added 3.0 pounds of dilinolamidopropyl dimethylamine (Phoenix Chemical Catemol 360). Stirring is continued at the same temperature for 20 minutes or until the amido amine co-emulsifier is completely dissolved. The emulsifier combination in the carrier is then ready for addition of water-insoluble silicone fluid. For example, 5 pounds of dimethicone/dimethiconol (Dow Corning Fluid Q2-1403) is added with rapid stirring while maintaining a temperature of about 160° F. Stirring is continued for 20 minutes or until the silicone fluid is completely dispersed and a homogeneous mix has been obtained. The resulting mix will comprise a stable emulsion of the silicone fluid. Thereafter, additional hair conditioning ingredients can be added, such as Quaternium-80, dimethicone copolyol, etc. For the addition of some of these ingredients, it may be desirable to reduce the temperature of the mix.

We claim:

1. A liquid hair care composition for conditioning hair with silicone oil, comprising a stable emulsion of a water-insoluble hair conditioning silicone oil dispersed in a liquid carrier composed essentially of polyoxyalkylene glycol selected from polyoxyethylene and copolymers of polyoxyethylene and polyoxypropylene, at least 60 parts by weight of said polyoxyalkylene glycol being present per 100 parts of said composition, and said composition further containing an effective emulsifying amount of a complex formed from (i) and anionic copolymer of dimethylpolysiloxane and polyoxyethylene wherein the siloxane chain contains from 20 to 40 dimethylsiloxy units and the oxyethylene chain contains from 3 to 15 oxyethylene units and terminates in an anionic phosphate or sulfate group, and (ii) a cationic hair conditioner compound which contains at least one cationic quaternary nitrogen or amido amine group and at least one hydrophobic aliphatic or silicone polymer chain.

2. The hair care composition of claim 1 in which from 0.8 to 1.2 mols of said cationic hair conditioner compound are present per mol of said anionic copolymer.

3. The hair care composition of claim 1 in which said polyoxyalkylene glycol is selected from the group consisting of polyoxyethylene glycol and copolymers of polyoxyethylene and polyoxypropylene, and in which the oxyethylene chain of said anionic copolymer terminates in an anionic phosphate group, and said cationic hair conditioner compound is selected from the group consisting of quaternary nitrogen-containing silicone polymers, fatty quaternary nitrogen compounds, and fatty amido amine compounds.

4. The hair care composition of claim 1 in which said oxyethylene chain terminates in an anionic phosphate group.

5. The hair care composition of claim 1 in which said oxyethylene chain terminates in an anionic sulfate group.

6. The hair care composition of claim 1 in which said cationic hair conditioner is a quaternary nitrogen-containing silicone polymer.

7. The hair care composition of claim 1 in which said cationic hair conditioner is a fatty quaternary nitrogen compound.

8. The hair care composition of claim 1 in which said cationic hair conditioner is a fatty amido amine compound.

9. The hair care composition of claim 1 in which said cationic hair conditioner is a fatty amido amine dimer.

10. A liquid hair care composition for conditioning hair with silicone oil, comprising a stable emulsion of a water-insoluble hair conditioning silicone oil dispersed in a liquid carrier composed essentially of polyoxyethylene glycol, at least 60 parts by weight of said glycol being present per 100 parts of said composition, and said composition further containing an effective emulsifying amount of a complex formed from (i) an anionic copolymer of dimethylpolysiloxane and polyoxyethylene wherein the siloxane chain thereof contains from 25 to 35 dimethylsiloxy units and the oxyethylene chain containing from 4 to 10 oxyethylene units and terminates in an anionic phosphate group, and (ii) a cationic hair conditioner compound containing at least one cationic quaternary nitrogen or amido amine group and at least one hydrophobic aliphatic or silicone polymer chain.

11. The hair care composition of claim 10 in which from 0.8 to 1.2 mols of said cationic hair conditioner compound are present per mol of said anionic copolymer.

12. The hair care composition of claims 10 or 11 in which cationic hair conditioner compound is selected from the group consisting of quaternary nitrogen-containing silicone polymers, fatty quaternary nitrogen compounds, and fatty amido amine compounds.

13. The hair care composition of claim 10 in which said cationic hair conditioner compound is a fatty amido amine compound.

14. The hair care composition of claim 10 in which said cationic hair conditioner compound is a fatty amido amine dimer.

15. The hair care composition of claim 10 in which said composition contains from 60 to 98 parts by weight of said polyoxyethylene glycol per 100 parts of the composition.

16. The hair care composition of claim 10 in which said composition contains from 60 to 98 parts by weight of said polyoxyethylene glycol together with 1 to 10 parts of said emulsifier complex and from 1 to 10 parts of said silicone oil.

* * * * *

UNITED STATES PATENT AND TRADEMARK OFFICE
CERTIFICATE OF CORRECTION

PATENT NO. : 5,332,569
DATED : July 26, 1994
INVENTOR(S) : James L. Wood
             Andrea Mariahazy It is certified that error appears in the above-indentified patent and that said Letters Patent is hereby corrected as shown below:

Column 3, lines 26-30:

In Formula (1), a bond (connecting line) should be present between the "P" and "O". Similarly, in Formula (2) a bond (connecting line) should be present between the "S" and the "O".

Signed and Sealed this

Fourth Day of October, 1994

Attest:

BRUCE LEHMAN

Attesting Officer        *Commissioner of Patents and Trademarks*